United States Patent [19]

Nakamura

[11] Patent Number: 4,892,191

[45] Date of Patent: Jan. 9, 1990

[54] CONTAINER HAVING INJECTION NEEDLE-DETACHING MEANS

[75] Inventor: Motohiko Nakamura, Kamakura, Japan

[73] Assignee: Nissho Corporation, Osaka, Japan

[21] Appl. No.: 368,888

[22] Filed: Jun. 20, 1989

Related U.S. Application Data

[63] Continuation of Ser. No. 225,985, Jul. 29, 1988, abandoned.

[30] Foreign Application Priority Data

Jul. 31, 1987 [JP] Japan ............................................. 117564

[51] Int. Cl.$^4$ ...................... B65D 25/00; B65F 1/02; B65F 7/00
[52] U.S. Cl. .................................... 206/366; 206/63.5
[58] Field of Search ...................... 206/365, 366, 63.5; 225/93

[56] References Cited

U.S. PATENT DOCUMENTS

| 4,466,538 | 8/1984 | Gianni ............................ 206/370 X |
| 4,802,579 | 2/1989 | Hall et al. .......................... 206/366 |
| 4,807,344 | 2/1989 | Kelson et al. ................... 206/366 X |

FOREIGN PATENT DOCUMENTS

| 0136392 | 1/1984 | European Pat. Off. . |
| 8614635 | 10/1986 | Fed. Rep. of Germany . |
| 8708179 | 10/1987 | Fed. Rep. of Germany . |
| 6045361 | 4/1984 | Japan . |

| WO82/00412 | 8/1980 | World Int. Prop. O. . |
| WO88/00067 | 1/1988 | World Int. Prop. O. . |

Primary Examiner—Allen M. Ostrager
Attorney, Agent, or Firm—Armstrong, Nikaido, Marmelstein, Kubovcik & Murray

[57] ABSTRACT

A container having an injection needle-detaching means for containing used injection needles comprising: a closed container for containing injection needles, and a needle-detaching means for detaching a slip type injection needle from a syringe, said needle-detaching means comprising a first opening provided in a wall of said container for inserting said needle attached to said syringe, a second opening extending laterally from said first opening, and a sliding portion provided on each of both sides of said second opening, said first opening having a size larger than the largest part of said needle, said second opening having a width larger than the diameter of the nozzle of said syringe and smaller than the diameter of the hub of said needle, each sliding portion having a wedge-like shape. When the nozzle portion of a syringe to which a slip type needle is attached is inserted into the second opening, each sliding portion is inserted into the spacing between the shoulder portion of the injection barrel and the bottom end of the hub of the needle like a wedge, thereby separating the needle from the nozzle. By using the container, the slip type needle can be detached from the syringe with safety without touching the needle with finger and contained directly thereinto.

4 Claims, 4 Drawing Sheets

CONTAINER HAVING INJECTION NEEDLE-DETACHING MEANS

This application is a continuation-in-part of application Ser. No. 225,985 filed July 29, 1989 now abandoned.

BACKGROUND OF THE INVENTION

The present invention relates to a container having an injection needle-detaching means for containing used injection needles. More particularly, the present invention relates to a container for detaching a used needle from a syringe with safety without touching the needle with finger and containing the detached needle directly therein.

The container of the present invention is applicable to a slip type needle. The slip type needle is one wherein a needle has a hub with a plain inner surface and the hub is simply forced to be put on the nozzle portion of a syringe that has a plain outer surface.

Conventionally, the injection needle was detached from the syringe by simply pulling out it with holding the hub thereof with fingers. At the first glance, such detaching operation appears to be easy. However, an accident that finger is injured with the needle inevitably happens when the same person repeats the needle-detaching operation several tens times or more a day.

Recently diseases infectious through blood such as viral hepatitis and acquired immuno-deficiency syndrome (AIDS) have increased rapidly. For the reason, it is important that persons who are engaged in test for the diseases and treatment of the diseases get out of direct touch with the blood of patients.

However, when a used needle is detached from a syringe in the conventional manner, there is a great possibility that a person gets hurt in the finger with the needle and the blood attached to the needle is entered into the body of the person through the wound so that the person is infected with the above-mentioned disease.

Accordingly, there is a demand for a means of detaching the needle from the syringe without touching the needle with finger.

With respect to blood-drawing needle which generally has two needles extending in the opposed directions from the hub, a needle-receiving container in compliance with the demand is proposed, as disclosed in U.S. Pat. No. 4,466,538. The container is provided with a slot which has a large width at one end and is narrowed toward the other end. A blood-drawing needle attached to a syringe is inserted into the wide portion of the slot and then moved toward the narrow portion, thereby catching the hub of the needle between both the side walls of the narrow portion. When the syringe is turned in such a state, the engagement between the syringe and the needle is loosened, so that the needle falls into the container.

However, the container has a drawback that since the hub of the needle is firmly caught between the side walls when the syringe is turned, the needle tends to remain in that position without falling into the container and the operator gets hurt in the finger with the needle when he touches the needle to remove the caught needle.

It is an object of the present invention to provide a container capable of detaching a slip type needle from a syringe with an easy operation without touching the needle with finger and containing the detached needle directly therein.

This and other objects of the present invention will become apparent from the description hereinafter.

SUMMARY OF THE INVENTION

The present invention provides a container having an injection needle-detaching means for containing used injection needles comprising:

a closed container for containing injection needles, and a needle-detaching means for detaching a slip type injection needle from a syringe, said needle-detaching means comprising a first opening provided in a wall of said container for inserting said needle attached to said syringe, a second opening extending laterally from said first opening, and a sliding portion provided on each of both sides of said second opening, said first opening having a size larger than the largest part of said needle, said second opening having a width larger than the diameter of the nozzle of said syringe and smaller than the diameter of the hub of said needle, each of said sliding portion having a side wall defining said second opening, each of said side walls having, at the entrance of the second opening from said first opening, a thickness smaller than a distance between the root of the nozzle of said syringe and the bottom end of the hub of said needle when the needle is being attached to said syringe, each of said side walls being made gradually thicker toward the closed end of said second opening, the maximum thickness of each side wall being larger than said distance.

DETAILED DESCRIPTION

First a syringe and an injection needle are explained in order to give a better understanding of the description hereinafter.

Figure 8:
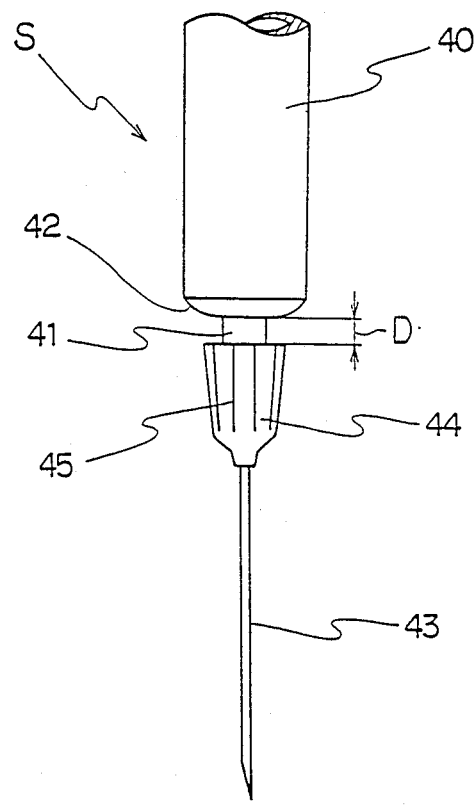
FIG. 8 is an explanatory view showing a syringe.

Referring to FIG. 8, the numeral 40 indicates a barrel of a syringe S. The syringe barrel 40 has a nozzle 41 at one end. The numeral 42 indicates a shoulder portion at the root of the nozzle 41. The numeral 43 indicates an injection needle and the injection needle 43 extends from a hub 44. In the case of the slip type needle, the hub 44 has a cavity with a plain inner surface and the corresponding nozzle 41 also has a plain outer surface. Plural ribs 45 may be provided on the outer surface of the hub 44 in the longitudinal direction thereof for the purpose of providing a moderate fitting strength between the hub 44 and a protector for the needle 43.

Referring to FIGS. 1 to 7, an embodiment of a container in accordance with the present invention will be explained.

Figure 1:
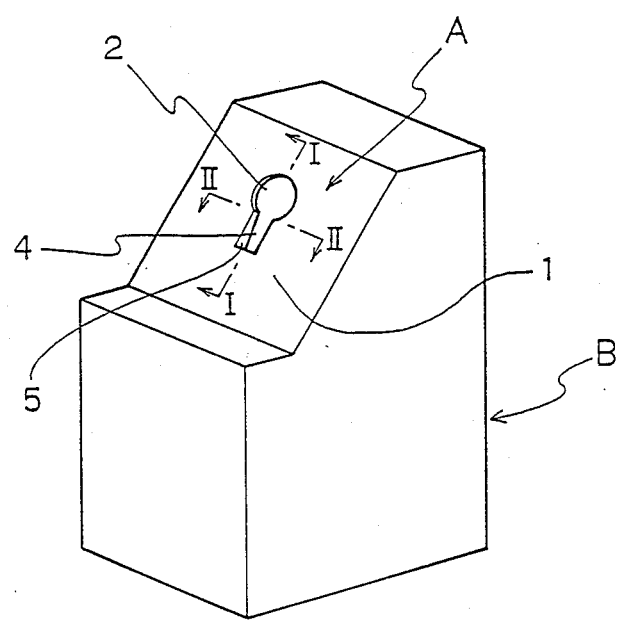
FIG. 1 is a perspective view showing a container in accordance with an embodiment of the present invention.

FIG. 1 shows a container B for used needles in which a needle-detaching means A is provided.

The means A is provided in an inclined wall of the container B. Needles detached from syringes by means of the means A are contained within the container B.

The construction of the container B is not limited to that illustrated in FIG. 1. The container B is made of wood, plastics, metal, etc. In the example shown in FIG. 1, the needle-detaching means A is provided only in one wall of the container B. However, a plurality of the means A may be provided in two or more walls of the container 8.

The means A comprises a first opening 2 for inserting an injection needle provided in a wall 1 of the container B and a second opening 4 extending laterally from the needle-inserting opening 2 and communicating with the opening 2, and a sliding portion 5 provided on each of both sides of the second opening 4.

The needle-inserting opening 2 has a size larger than the largest part of an injection needle 43. Usually the largest part is a hub 44. However, when a protector is put on the needle 43, the largest part is the protector if the diameter of the protector is larger than that of the hub 44. Preferably the opening 2 has a size smaller than the diameter of the barrel 40 of the syringe S.

Figure 5:
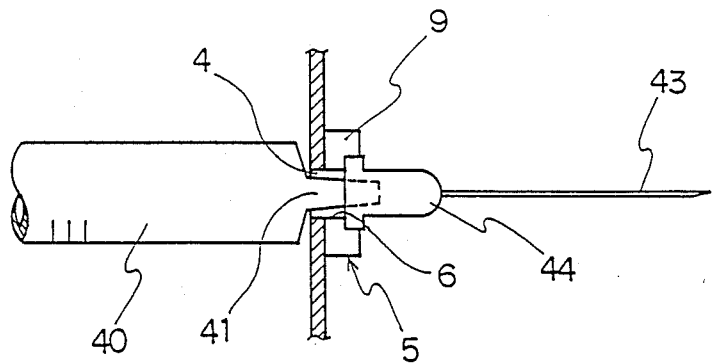
FIG. 5 is a partial sectional view showing the same state as illustrated in FIG. 4, but corresponding to a section taken along with the line II—II.
Figure 7:
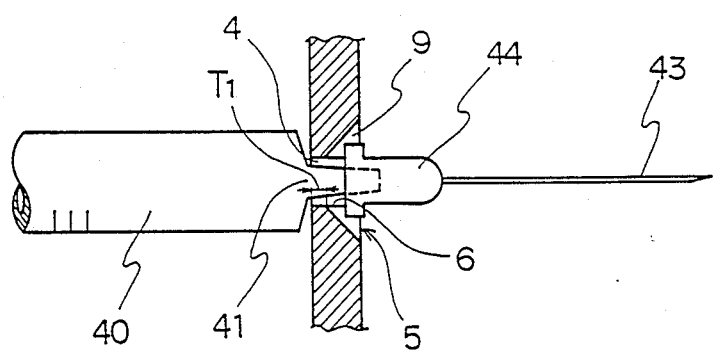
FIG. 7 is a partial sectional view showing the same state as illustrated in FIG. 6, but corresponding to a section taken along the line II—II in FIG. 1.

The second opening 4 has a width larger than the diameter of the nozzle 41 of the syringe S and smaller than the diameter of the hub 44, as shown in FIG. 5 and FIG. 7.

Each of the sliding portions 5 has a side wall 6 defining the second opening 4.

Each side wall 6 has, at the entrance 7 of the second opening 4 from the first opening 2, a thickness $T_1$ smaller than a distance D between the root of the nozzle 41 and the bottom end of the hub 44 when the needle 43 is being firmly attached to the syringe S, and each side wall 6 is made gradually thicker toward the closed end 8 of the second opening 4 and the maximum thickness $T_2$ of each side wall 6 at the closed end 8 is larger than the distance D, as shown in FIGS. 2, 3, 4 and 6.

The shape of the second opening 4 is usually a rectangle in plane as shown in FIG. 1. However, the width of the second opening 4 may be made smaller toward the closed end 8. Further, the length of the second opening 4 may be reduced so that the plane shape becomes similar to a regular square.

Figure 2:
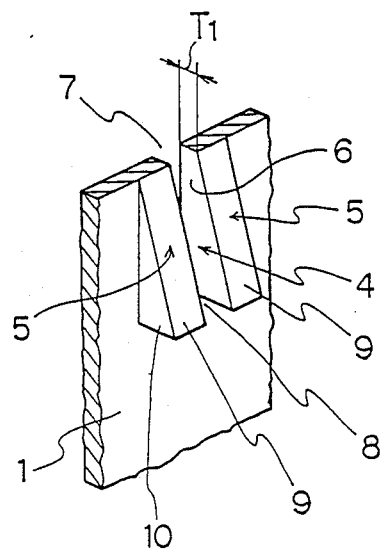
FIG. 2 is a partially broken, enlarged perspective view showing an example of the needledetaching means of the container shown in FIG. 1, viewed from the inside of the container.
Figure 4:
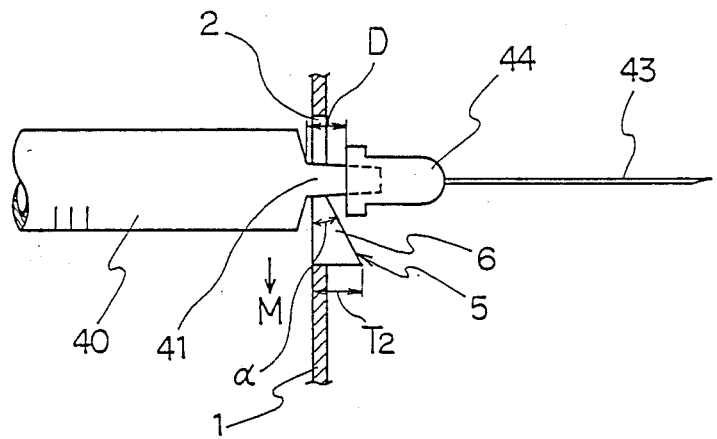
FIG. 4 is a partial sectional view showing a state wherein a syringe is inserted in the needledetaching means shown in FIG. 2, corresponding to a section taken along the line I—I in FIG. 1.

In the case of an example of the needle-detaching means A as shown in FIGS. 2, 4 and 5, the side wall 6 has the same thickness $T_1$ as that of the wall 1 at the entrance 7 but the remaining parts of the side wall 6 are thicker than the wall 1. The surface 9 of the sliding portion 5 on the rear side of the wall 1 constitutes a sliding surface on which the bottom surface of the hub 44 slides. Both sliding surfaces 9, 9 are flush with each other. The sliding portion 5 as shown in FIGS. 2, 4 and 5 is formed by providing a wedge-like portion 10 on each of both sides of the second opening 4 on the rear side of the wall 1 so that the surface of the wedge-like portion which inclines in the direction of the first opening 2 constitutes the sliding surface 9.

Figure 3:
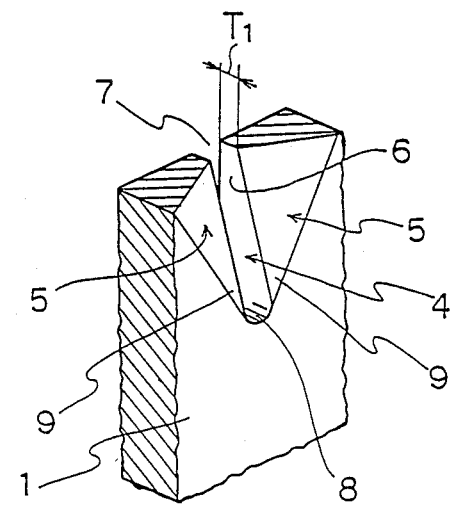
FIG. 3 is a partially broken, enlarged perspective view showing another example of the needledetaching means, viewed from the inside of the container.
Figure 6:
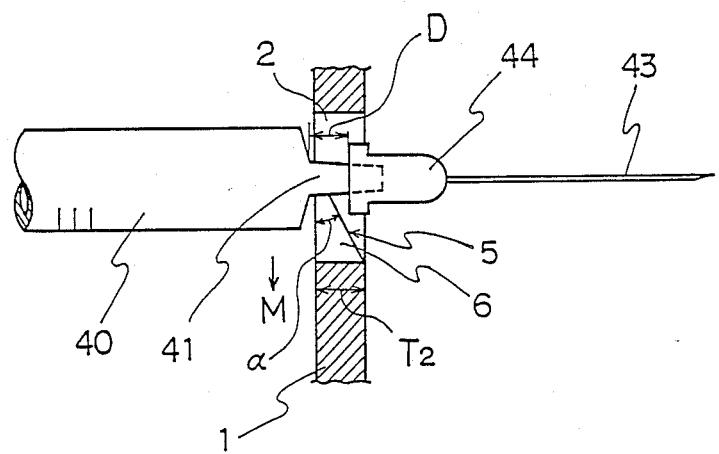
FIG. 6 is a partial sectional view showing a state wherein a syringe is inserted in the needledetaching means shown in FIG. 3, corresponding to a section taken along the line I—I in FIG. 1.

In the case of another example of the needle-detaching means A in FIGS. 3, 6 and 7, the side wall 6 has the same thickness $T_2$ as that of the wall 1 at the closed end 8 but the remaining parts of the side wall 6 are thinner than the wall 1. The surface 9 of the sliding portion 5 on the rear side of the wall 1 constitutes a sliding surface on which the bottom surface of the hub 44 slides. Each sliding surface 9 is inclined both in the direction of the first opening 2 and in the direction of the second opening 4. The sliding portion 5 as shown in FIGS. 3, 6 and 7 is formed by cutting off the rear side of the wall 1 on each of both sides of the second opening 4 so as to incline both in the direction of the first opening 2 and in the direction of the second opening 4 so that the inclined surface constitutes the sliding surface 9.

The side wall 6 must have a maximum thickness $T_2$ sufficient to remove the hub 44 from the nozzle 41. The maximum thickness $T_2$ is larger than a distance D between the root of the nozzle 41 and the bottom surface of the hub 44 to surely detach the hub 44 from the nozzle 41.

Further the angle $\alpha$ between both edge lines of the side wall 6 in the longitudinal direction of the second opening 4 is preferably from 5° to 45°, more preferably from 15° to 30°, to facilitate a smooth removal of the hub 44 from the nozzle 41.

The needle-detaching operation using the needle-detaching means A shown in FIG. 2 will be explained by referring to FIGS. 4 and 5.

FIG. 4 and FIG. 5 are a sectional view taken along the line I—I of FIG. 1 and a sectional view taken along the line II—II of FIG. 1, respectively, when the syringe S is positioned on the line II—II of FIG. 1.

The lower portion of the syringe S to which the needle 43 is attached is inserted into the first opening 20 until the shoulder portion 42 of the barrel 40 is brought into contact with the pheriphery of the first opening 2 and then moved into the second opening 4, followed by further movement toward the closed end 8. When the syringe S is moved toward the closed end 8 in the direction of the arrow M, both side walls 6, 6 are inserted into the spacing between the shoulder portion 42 of the barrel 40 and the bottom surface of the hub 44 like a wedge because of increasing thickness of each side wall 6. As a result, the hub 44 is pushed downward so that it is loosened and finally separated from the nozzle 41.

The needle-detaching operation using the needle-detaching means A shown in FIG. 3 will be explained by referring to FIGS. 6 and 7.

FIG. 6 and FIG. 7 are a sectional view taken along the line I—I of FIG. 1 and a sectional view taken along the line II—II of FIG. 1, respectively, when the syringe S is positioned on the line II—II of FIG. 1.

The needle-detaching means A in FIG. 3 is preferably used when the thickness of the wall 1 is larger than the distance D between the root of the nozzle 41 and the bottom surface of the hub 44.

The lower portion of the syringe S to which the needle 43 is attached is inserted into the first opening 2 until the shoulder portion 42 of the barrel 40 is brought into contact with the pheriphery of the first opening 2 and then moved into the second opening 4. Both side walls 6, 6 are inserted into the spacing between the shoulder portion 42 of the barrel 40 and the bottom surface of the hub 44 at the entrance 7. When the syringe S is further moved toward the closed end 8 of the second opening 4, the hub 44 is gradually spaced apart from the shoulder portion 42 of the barrel 40 and finally separated from the nozzle 41, the separated needle 43 falling within the container B.

When used needles are accumulated in the container B, the container B is closed and subjected to a discarding treatment such as burning.

By using the needle-detaching means A of the present invention, a needle to which blood is attached can be detached smoothly from a syringe with an easy operation without touching the needle with the hand.

Further, the side walls are inserted into the spacing between the shoulder portion of the barrel and the bottom surface of the hub like a wedge, so that the hub is spaced apart from the nozzle and finally separated from the nozzle. Accordingly, there does not occur the problem of the conventional device that since the needle is caught in the device because of twisting the hub thereof to loosen it, a person such as doctor must remove the caught needle from the device by touching it with the hand, and there is no danger of infection.

The container B having the means A can be manufactured by a conventional method. For instance, when a resin material is used, it can be produced by injection-molding.

A container having the needle-detaching means A may be formed integrally as a whole from a resin by a conventional molding method such as injection molding. Examples of the resin include polyethylene, polypropylene, acrylonitrile-butadiene-styrene copolymer, polycarbonate and polyester. A wall member having the needle-detaching means A may be formed integrally as a whole from a resin or other material and the wall member is installed to a container produced separately. The needle-detaching means A may be formed in a container or a wall member thereof separately produced. That is, the first opening 2 and the second opening 4 are formed in a wall of the container or the wall member. In the case of the needle-detaching means A shown in FIG. 2, a separately produced wedge-like member corresponding to the wedge-like portion 10 is attached to both sides of the second opening 4 on the rear side of the wall 1 so that the sliding surface 9 inclined in the direction of the first opening 2 is provided. In the case of the needle detaching means A shown in FIG. 3, the rear side of the wall 1 on each of both sides of the second opening 4 is cut off so that the sliding surface 9 inclined both in the direction of the first opening 2 and in the direction of the second opening 4 is provided. The means A is preferably provided in the container B so that the barrel 40 can be moved downward as shown in FIG. 1 because it is easy to apply force on the barrel 40.

In addition to the elements used in the Examples, other elements can be used in the Examples as set forth in the specification and the drawings to obtain substantially the same results.

What is claimed is:

1. A container having an injection needle detaching means for containing used injection needles comprising:
   a closed container for containing injection needles, and
   a needle-detaching means for detaching a slip type injection needle from a syringe,
   said needle-detaching means comprising a first opening provided in a wall of said container for inserting said needle attached to said syringe, a second opening extending laterally from said first opening, and a sliding portion provided on each of both sides of said second opening,
   said first opening having a size larger than the largest part of said needle,
   said second opening having a width larger than the diameter of the nozzle of said syringe and smaller than the diameter of the hub of said needle,
   each of said sliding portion having a side wall defining said second opening,
   each of said side walls having, at the entrance of the second opening from said first opening, a thickness smaller than a distance between the root of the nozzle of said syringe and the bottom end of the hub of said needle when the needle is being attached to said syringe, each of said side walls being made gradually thicker toward the closed end of said second opening, the maximum thickness of each side wall being larger than said distance, the surface of said sliding portion on the rear side of said wall of said container, on which the bottom surface of the hub slides, forms a surface inclined both in the direction of the first opening and in the direction of the second opening.

2. The container of claim 1, in which the angle between both edge liens of each slide wall in the longitudinal direction of said second opening is from 5° to 45°.

3. The container of claim 1, in which each of said side walls has substantially the same thickness as that of said wall of said container at said entrance, and a wedge-like portion is provided on each of both sides of said second opening on the rear side of said wall of said container so that the surface of each wedge-like portion which inclines in the direction of the first opening constitutes said inclined sliding surface on which the bottom end of the hub slides.

4. The container of claim 1, in which said wall of said container has a thickness larger than said distance, and the rear side of said wall on each of both sides of said second opening is cut off and forms said inclined surface both in the direction of the first opening and in the direction of the second opening so that the inclined surface constitutes a sliding surface on which the bottom end of the hub slides.

* * * * *